United States Patent [19]

Dietwart

[11] Patent Number: 5,238,660
[45] Date of Patent: Aug. 24, 1993

[54] APPARATUS FOR CLEANING AND STERILIZING

[76] Inventor: Voelpel Dietwart, Villanystrasse 14, 8050 Freising/F.R., Fed. Rep. of Germany

[21] Appl. No.: 710,818

[22] Filed: Jun. 5, 1991

[30] Foreign Application Priority Data

Jun. 5, 1990 [DE] Fed. Rep. of Germany ........ 4018023
Jan. 2, 1991 [EP] European Pat. Off. ......... 91100026.3

[51] Int. Cl.⁵ .................................................. A61L 2/18
[52] U.S. Cl. ................................... 422/295; 422/297; 422/302; 422/303; 134/133; 134/153; 414/498
[58] Field of Search ............... 422/295, 297, 300, 302, 422/303; 134/133, 153; 414/149, 222, 287, 498

[56] References Cited

U.S. PATENT DOCUMENTS

| | | | |
|---|---|---|---|
| 3,853,622 | 12/1974 | Rutten | 134/153 |
| 3,895,911 | 7/1975 | Prins | 422/302 |
| 4,042,128 | 8/1977 | Shrader | 414/287 |
| 4,143,669 | 3/1979 | Minkin | 134/153 |
| 4,197,000 | 4/1980 | Blackwood | 134/153 |
| 4,236,541 | 12/1980 | Cipriani | 134/153 |
| 4,697,974 | 10/1987 | Eltoukhy | 414/498 |
| 4,739,782 | 4/1988 | Nourie | 134/153 |
| 4,744,379 | 5/1988 | Goettel | 134/133 |

FOREIGN PATENT DOCUMENTS 324855 7/1984 Fed. Rep. of Germany .

OTHER PUBLICATIONS

Fedegari Autoclave Catalogue, Nov. 1986.

*Primary Examiner*—Lynn M. Kummert
*Attorney, Agent, or Firm*—Helfgott & Karas

[57] ABSTRACT

An apparatus for cleaning and sterilizing objects, such as pharmaceutical caps, plugs and the like includes an autoclave chamber and a cleaning device having a cleaning drum mounted for a free rotation on a frame. The frame runs on rollers and can be moved in and out of the autoclave chamber. The cleaning drum has a hollow shaft provided within the drum with spray nozzles and mounted axially in line with a hollow drive shaft passing through one sidewall of the autoclave chamber free to turn and sealed. The drum shaft and the drive shaft may be coupled together by a coupling device. The frame may be released from the drum introduced into the autoclave chamber so that it is not located during the cleaning process in the autoclave chamber and thus will not constitute an additional source of contamination.

17 Claims, 5 Drawing Sheets

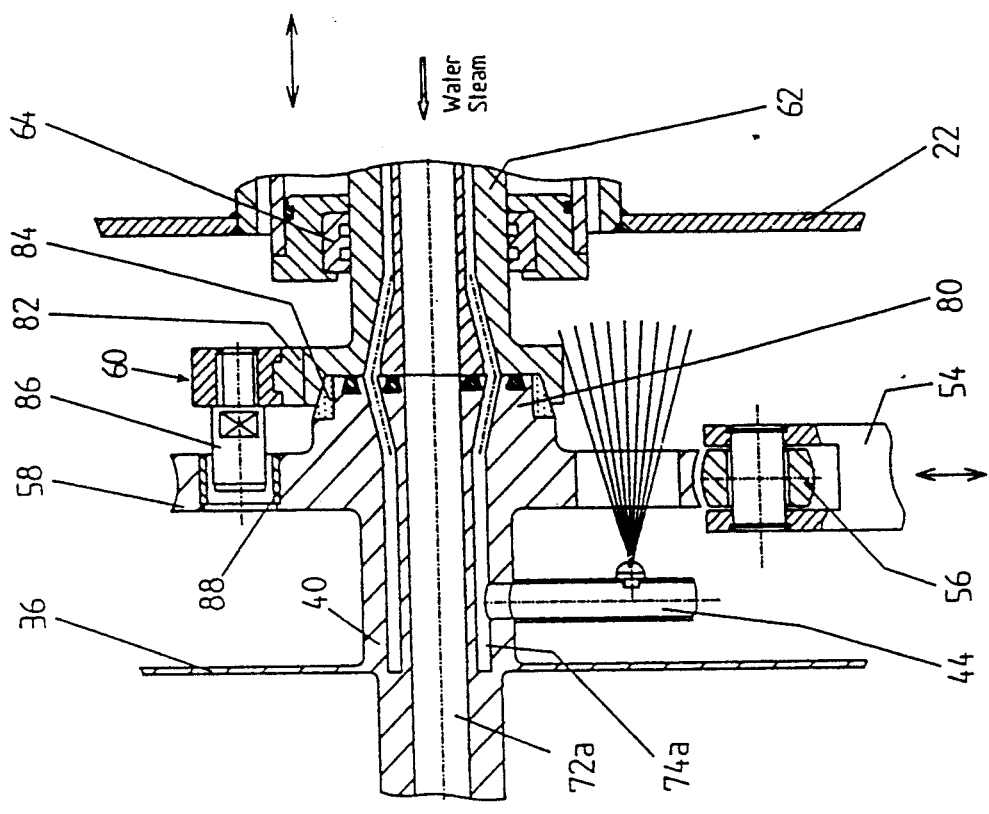
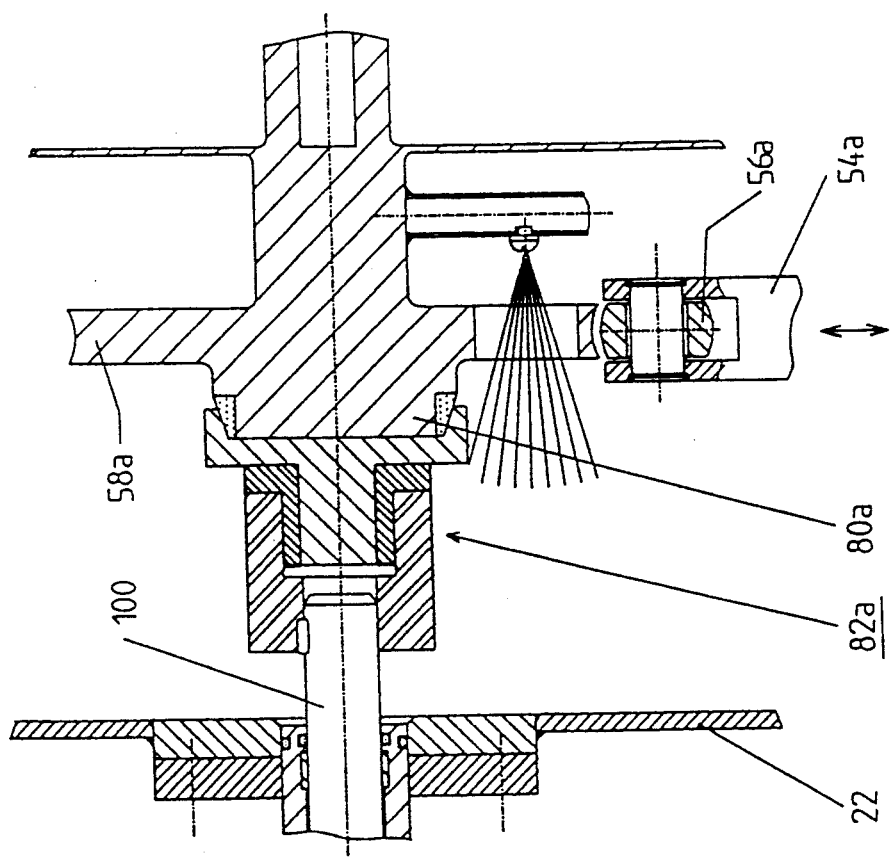
FIG. 7

APPARATUS FOR CLEANING AND STERILIZING

FIELD OF THE INVENTION

The present invention relates to an apparatus for cleaning and sterilizing objects, especially but not limited to such small items as closure elements for containers for pharmaceutical fluids e.g. caps, plugs and the like.

DESCRIPTION OF THE RELATED ART

The demands on the cleanliness, absence of particulates, and sterility of certain objects, particularly pharmaceutical caps and plugs and the like made e.g. of rubber or plastic materials, and other articles as used in pharmaceutical and medical applications are very high. Despite this, cleaning and sterilizing must be able to be implemented reliably and cost-effectively. German Patent 32 48 555 discloses a machine for cleaning sensitive small items, such as capping and plugging elements as used in pharmaceutical applications, which incorporates an external drum which is substantially closed and which is connected to feed and drain lines for treatment fluids. In the external drum an internal drum having a hollow shaft connected to a drive unit is rotably mounted. This hollow shaft is connected to means for feeding the cleaning fluid and has spray nozzles which spray into the interior of the internal drum. Also connected to this hollow shaft is a U-shaped spray pipe which surrounds U-shaped the internal drum in a plane passing through its turning axis and having spray nozzles which spray in the direction of the interior wall of the external drum. The external drum has a loading opening which can be sealed tight and which is accessible from a non-sterilized room, as well as an unloading opening which can be sealed tight and which is accessible from a sterilized room.

Autoclave systems are also known in which wheeled cleaning means containing a rotably mounted drum can be moved in the axial direction of the drum from a non-sterilized room into the system and in which the objects contained in the drum following cleaning and sterilization can be removed in a sterilized room.

The aforementioned prior art suffers from various drawbacks. In the first-mentioned machine the cleaning can only be done in the non-removably mounted drum, which is not suitable for cleaning objects accommodated in trays or cassettes since the external drum practically represents an autoclave. In addition, loading the drum cannot be commenced until it has been unloaded and it is not possible to swap the unloaded drum by a new loaded drum. In an apparatus containing an autoclave chamber and cleaning means which can be wheeled into the chamber, it is generally not possible to ensure adequate cleanliness and removal of particulate matter.

SUMMARY OF THE INVENTION

It is an object of the invention to provide an apparatus for cleaning and sterilizing such objects as pharmaceutical caps, plugs and the like, capable of satisfying the highest demands as to cleanliness, sterility, and absence of particulate matter, whilst ensuring easy, reliable and cost-effective operation.

The invention may be embodied in an apparatus comprising an autoclave chamber having a first-closure means for sealing off a loading opening in a first end wall, a second end wall opposite the first wall incorporating a second closure means, such as a lid, for sealing off an unloading opening and an enclosure wall, cleaning means which can be introduced into said autoclave chamber and comprising a frame for mounting a drum serving to accommodate the objects to be cleaned, having a foraminous circumferential wall and a shaft for mounting the drum and allowing the drum to turn in the frame, drive means arranged outside of said autoclave chamber to drive the drum and which can be coupled with the drum through an opening provided the first end wall of the autoclave chamber, and means for feeding at least one fluid such as a cleaning fluid into the autoclave chamber.

The drum shaft is a hollow shaft forming at least one fluid channel. The drive means comprises at least one driving hollow shaft separable from the drum shaft and passing sealed and rotatably through one end wall of the autoclave chamber. The coupling shaft is coupled to a driving unit outside of the autoclave chamber. When the cleaning means is arranged in the autoclave chamber, the drive shaft and the drum shaft are essentially axially alined and can be coupled and uncoupled by a pair of opposing, complementary coupling components for mechanical connection and for connecting fluid channels running through these shafts.

The present invention ensures optimum cleanliness and practically complete absence of particulate matter as well as satisfactory sterilization of objects, which can be implemented by a variety of methods as selected. Whilst one drum batch is being cleaned and sterilized, a second drum can be made ready and filled so that the first drum, after emptying, can be replaced by the filled, second drum, thus enabling a new cleaning and sterilization cycle to be commenced without delay. The autoclave chamber can also be used for cleaning objects accommodated in trays, troughs, cassettes and the like, or also for larger objects which e.g. can be wheeled into the autoclave on a suitable pallet or a dolly and the like. Since the hollow shaft of the drum and the drive shaft can be coupled together axially in line due to a simple, sealed coupling means, the risk of unwanted foreign particles entering the autoclave chamber due to the coupling means is more or less eliminated. Even when the autoclave chamber is used without the cleaning drum coupled, the remaining portion of the coupling means represents no risk of contamination. Apart from this the interior of the autoclave chamber can be speedily and effectively cleaned through the nozzles of the nozzled pipe which are oriented outwards. Since the autoclave chamber has practically no incorporated items, it can be used for a variety of purposes.

It is of particular advantage when the frame which mounts the cleaning drum for moving it in and out of the autoclave chamber (both through the loading opening at the non-sterilized end) can be uncoupled from the drum used in the autoclave chamber and can be removed from the latter independently of the drum so that the frame is not in the autoclave chamber during the cleaning process and thus will not constitute a source of contamination.

BRIEF DESCRIPTION OF THE DRAWINGS

Embodiments of the invention shall now be explained in the following with reference to the drawings, in which

FIG. 7 is an enlargened axial section of the apparatus shown in FIG. 6.

DESCRIPTION OF THE PREFERRED EMBODIMENTS

Figure 1:
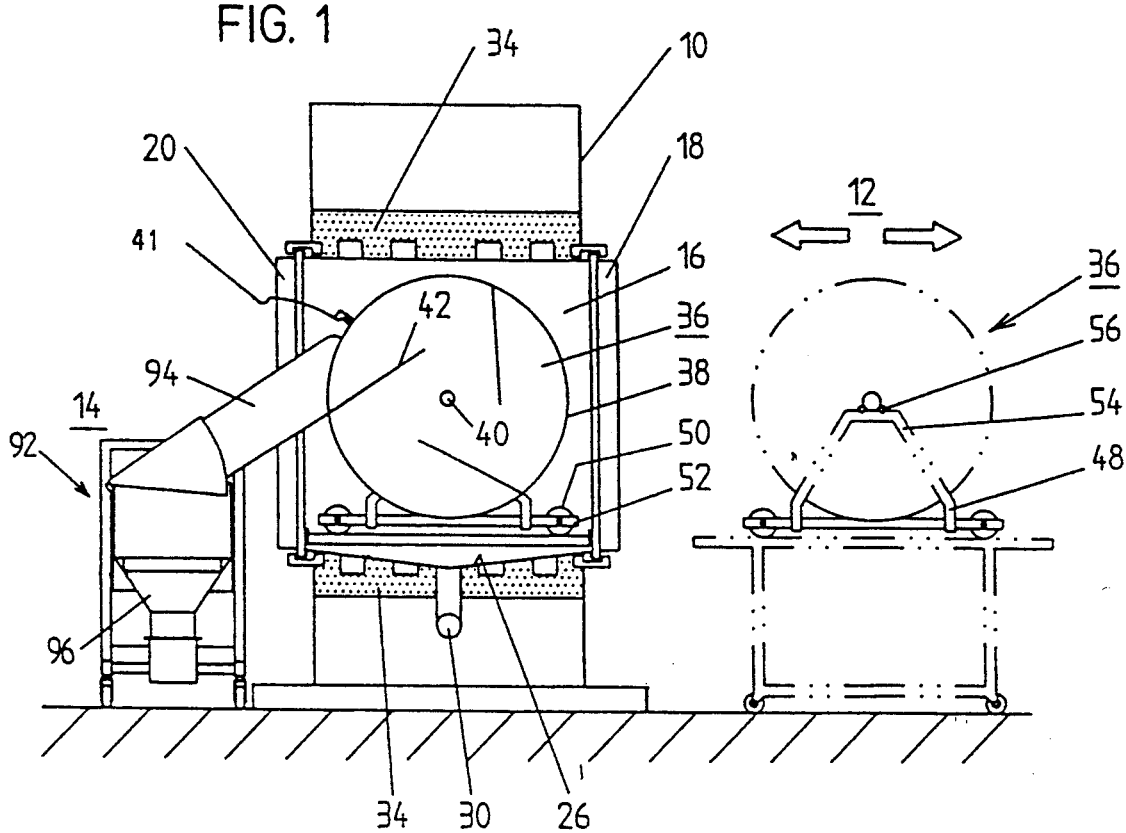
FIG. 1 is a schematic, partial-section side view of an apparatus according to one embodiment of the invention.
Figure 2:
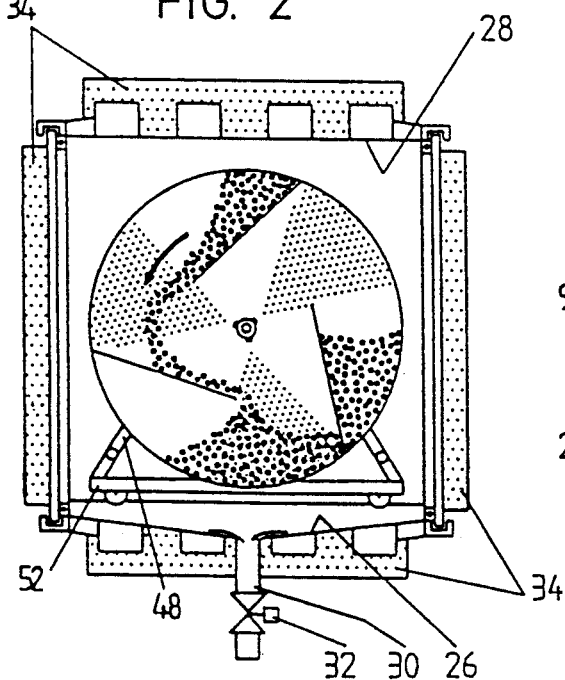
FIG. 2 is a schematic cross-section through an autoclave chamber of the apparatus of FIG. 1 and cleaning means moved into same.

FIGS. 1 to 5 show a first embodiment of an apparatus according to the invention for cleaning and sterilizing pharmaceutical capping elements such as rubber plugs or bungs. It can, of course, also be used for the treatment of other objects, as well as for other fluid treatment procedures, such as silicon coating, where the demands on cleanliness are correspondingly high. The apparatus as shown contains a housing 10 which separates an unclean room 12 from a clean, i.e. sterile room 14. In the housing 10 an autoclave chamber 16 is provided, having at its first end a loading opening which can be sealed off tight by sealing means which is shown for the sake of simplicity as a door 18, and at its opposite end an unloading opening which can also be sealed off tight by sealing means again shown as a door 20. The autoclave has further two sidewalls 22, 24 ( FIG. 3), a floor 26 and a top wall 28. The floor 26 (FIGS. 1 and 2) is funnel-shaped and has a drain pipe 30 at its lowest point, which can be closed off by a valve 32, particularly by a solenoid valve. In the embodiment shown, the floor, ceiling and doors are each provided with heating means and/or thermal insulation 34 indicated merely schematically in the drawings.

The apparatus further comprises cleaning means 36 which can be moved into the autoclave chamber 16 from the side of the unclean room 12. These cleaning means includes in the present embodiment a cleaning drum 38 with a foraminous circumferential wall and a door 41 for loading and unloading the drum. The drum 38 receives the objects to be cleaned and is seated on a hollow shaft 40 serving as a nozzle pipe and having nozzles which spray outwards to furnish a fan-shaped jet of fluid as represented by the dotted sectors in FIG. 2. In the drum three baffle plates 42 are arranged at an angle of approx. 20° to the radial direction. Substantially the drum is conventional and configured e.g. as described in the aforementioned German Patent.

Figure 3:
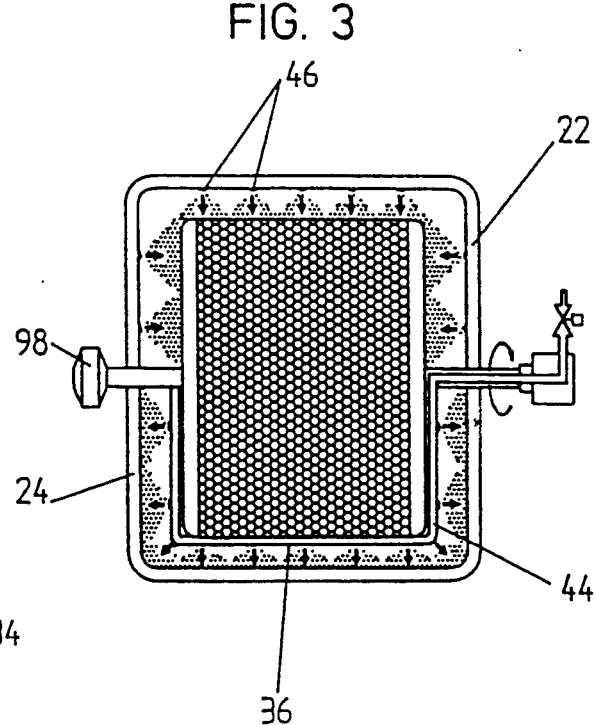
FIG. 3 is a schematic side view of the autoclave chamber of FIG. 2 in a plane of the axis of a cleaning drum.

As shown in FIG. 3, a U-shaped nozzle pipe 44 is connected to the hollow shaft, this pipe running in the plane passing through the axis of the drum and having spray nozzles set to spray inwards by means of which the exterior of the drum 38 or other objects located within the autoclave chamber can be cleaned. On the interior wall of the autoclave chamber spray nozzles 46 (FIG. 3) are provided to spray inwards in the direction of the drum 38 and which are connected to a suitable fluid feed (not shown).

Figure 4:
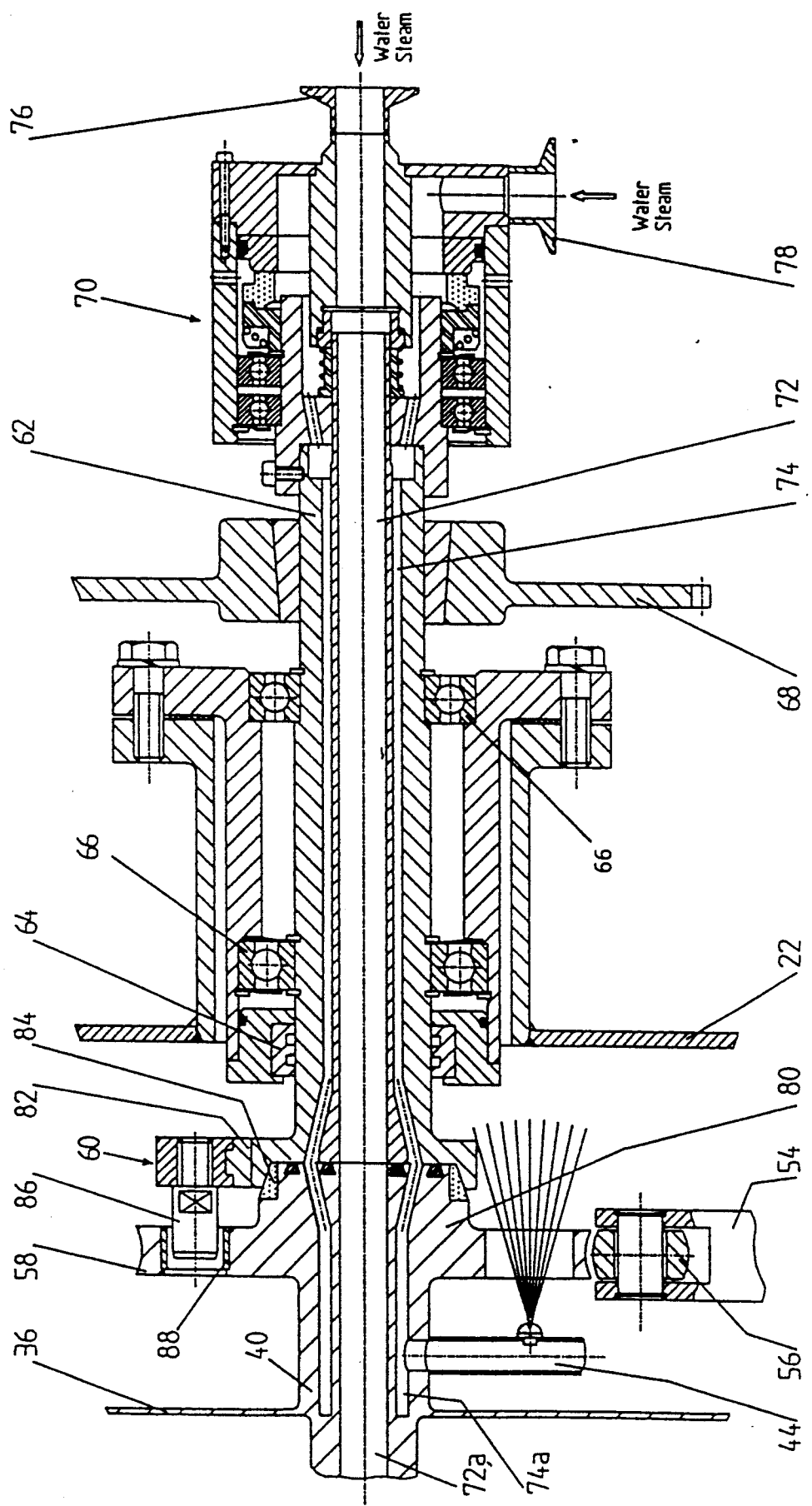
FIG. 4 is an enlargened axial section through a part of the apparatus shown in FIGS. 1 to 3.

The cleaning means 36 has a frame 48 having a baseframe 52 wheeled by four rollers 50 in FIG. 1 and two upright brackets 54 roughly trapezoidally shaped, at the upper end of which the hollow shaft 40 is mounted free to rotate about an axis running at right angles to the direction of movement of the rollers 50. For this purpose the brackets 54 are each provided at the top with two bearing rollers 56 located one alongside the other. FIG. 4 shows the one end of the drum. The bearing rollers 56 are slightly convex-shaped at the end at which a bearing disk 58 connected to the hollow shaft 40 runs, this disk having a suitably concave-shaped end. The bearing means at the other end of the drum is configured accordingly. Grooves or rails for guiding the rollers 56 are suitably provided on the floor of the autoclave chamber 16 to ensure precise positioning of the cleaning means 36 in the autoclave chamber in the axial direction of the drum 38.

The hollow shaft 40 has a releasable coupling means 60 (explained in more detail below, with reference to FIGS. 4 and 5) by means of which it can be coupled to a hollow drive shaft 62 both mechanically and fluidly with respect to the fluid channels running in the hollow shafts 40, 62. The drive shaft 62 is relative to the sidewall 22 sealed off pressure and vacuum tight e.g. by a labyrinth-type seal 64 and mounted free to rotate outside of the seal 64 in roller bearings 66. The shaft 62 is driven via a gearwheel 68 by a variable-speed reversible drive means (not shown) which may contain a gearbox and an electric motor.

At the outer end of the drive shaft 62 a rotary head 70 of the known kind is provided. In the embodiment shown, the drive shaft 62 forms a central fluid channel 72 and at least one additional fluid channel 74 out of axial alignment in connection with separate fluid ports 76 and 78, respectively of the rotary head 70, each of which permits the introduction of such treatment fluids as water, steam, leachant, silicon coating fluid, and/or sterilizing gas such as ethylene oxide and the like.

The coupling means incorporates a taper end 80 connecting the hollow shaft 40 of the cleaning drum, of relatively slight conicity. The drive shaft 62 has at its internal end a coupling member 82 which has a concave shape complementary to that of the taper end 80. The fluid channels 72 and 74 merge in the concave section of the coupling member 82 and the taper end 80 into suitable channels 72a, 74a forming the continuation of the channels 72 and 74 respectively, 72a channel feeds the nozzles of the drum shaft 40 and channel 74a the nozzles of the nozzle pipe 44. For sealing, member 80 has an outer ring-shaped seal 84 with a tapered outer surface, together with two O-ring seals, arranged without and within the merging of the outer-axial fluid channel 74.

The coupling means 60 further includes a driven pin 86 secured in a radial projection of the coupling member 82 and which mates with a hole 88 in the bearing disk 58 when the coupling means is engaged.

Figure 5:
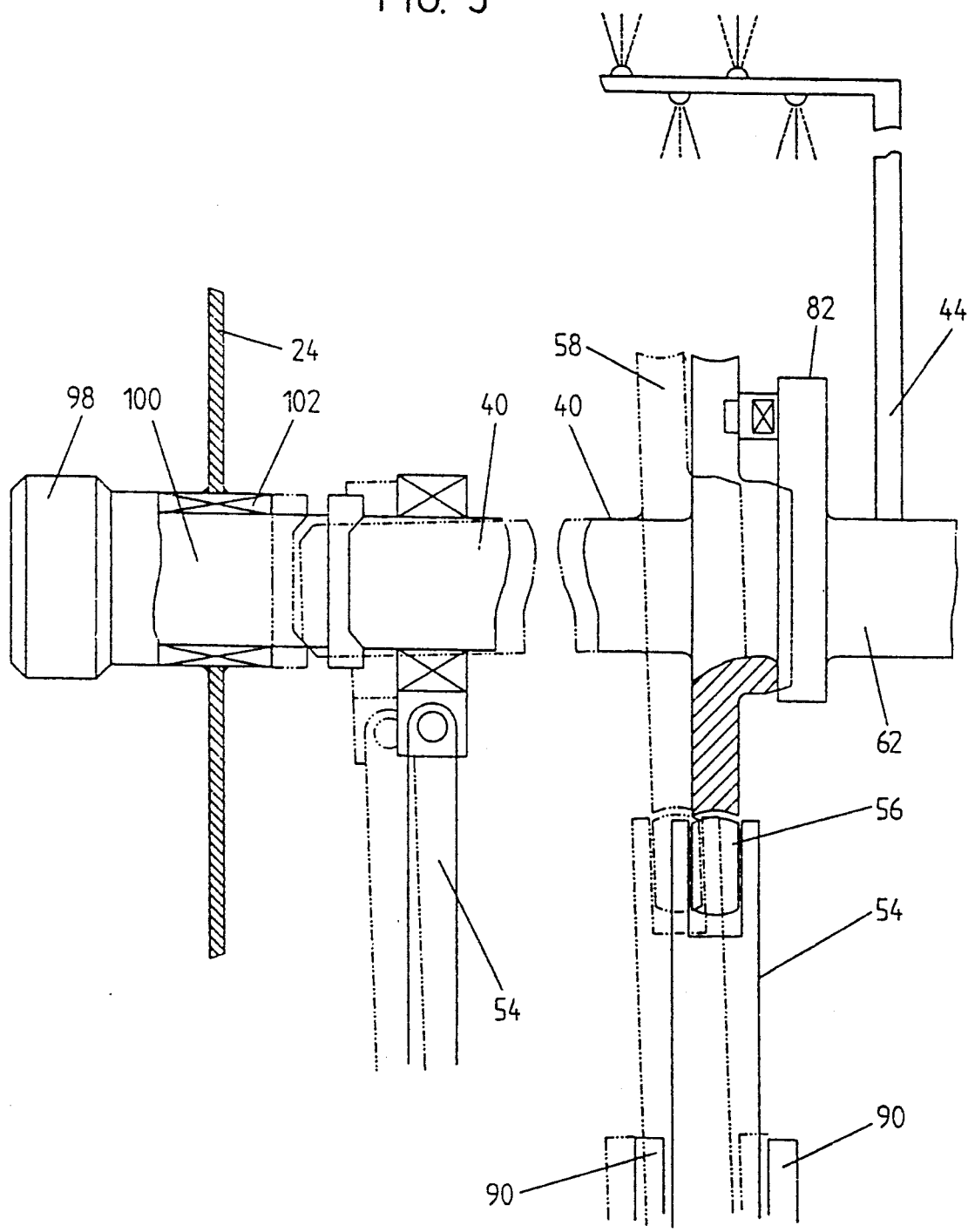
FIG. 5 is a schematic view of a coupling means of the apparatus shown in FIGS. 1 to 4.

Engaging and disengaging of the coupling means 60 can be done in various ways. As FIG. 5 shows the brackets 54 or part of them in the embodiment as shown can be swivelled in the axial direction of the drum about a small angle so that the hollow shaft 40 together with the drum can be shifted away from the axially fixed member of the coupling 82 sufficiently so that the taper end 80 and the driven pin 86 do not obstruct forward and reverse movement of the cleaning means 36. The swivel range of the brackets 54 is limited by a stop 90 which is secured to the frame by means which are not shown. The swivel movement between the released (disengaged) position (shown dashed in FIG. 5) and the engaged position (shown solid line in FIG. 5) is implemented in the embodiment according to FIG. 5 by a pneumatic cylinder 98 which permits shifting a shaft 100 axially, this shaft being mounted free to turn and axially shiftable and tight in the side wall 24 of the autoclave chamber 16 by a suitably sealed bearing means 102. The shaft 100 is—at least in the engaged position—in axial alignment with the drum shaft 40 on which it exerts such a high axial force that the required seal of the coupling means 36 is ensured at the fluid pressures employed. The arrangement of the swivel axes of the brackets 54, the length of the swivelling parts of the brackets and the range of swivel are all dimensioned to advantage so that the bearing disk 58 is lifted off the rollers 56 when the tapered coupling members are pressed together, thus eliminating abrasion in operation at the rollers and bearing disk. The same applies correspondingly to the bearing disk located at the other end of the drum when the drum runs in bearings as shown in FIG. 4. Alternatively the drum shaft 40 can also run in plain bearings at one or both ends of the shaft, as shown for the left-hand end of the drum shaft 40 in FIG. 5. The shaft 100 may be a hollow shaft and, like the drive shaft 62, coupled to a drive means and/or provided with a rotary head so that from this end too, fluids can be fed into the system.

Alternatively the coupling means can also be made so that the drive shaft 62 can be mounted to permit axial shifting to enable the coupling to be engaged and disengaged. In this case a counterbearing of the rotary type may be provided at the opposite end of the drum shaft to take the axial force necessary for sealing the coupling means 60. The drive shaft may also feature a mechanical seal or may be sealed by a bellows-type seal of red brass.

In a different version of the aforementioned embodiment the U-shaped nozzle pipe 44 is not connected to the hollow shaft 40 but to the part of the drive shaft 62 projecting into the interior of the autoclave chamber. This has the advantage that the nozzle pipe 44 is also available for cleaning and treatment purposes should some other cleaning means be used different from the drum cleaning means 36 as described. In this case, it is then possible to clean e.g. objects accommodated on a pallet or in trays when moved into the autoclave chamber by means of the spray nozzles of the nozzle pipe 44 which are directed inwards, the turning range of the nozzle pipe 44 then, of course, being suitably limited e.g. to over 180°.

In yet a further embodiment of the present cleaning means the autoclave chamber may be provided with means (not shown) for feeding microwave energy, these means being similar to those used in popular microwave cookers.

For unloading there is no need to remove the drum cleaning means 36 from the autoclave chamber, instead it is sufficient—as shown by FIG. 1—to provide at the sterile end, unloading means 92 incorporating a chute 94 and a receiving vessel 96 connected to the drum and to drive, if necessary a number of times, the drum clockwise, i.e. in the opposite direction to that of cleaning ( FIG. 2) and to open the drum door 41.

Figure 6:
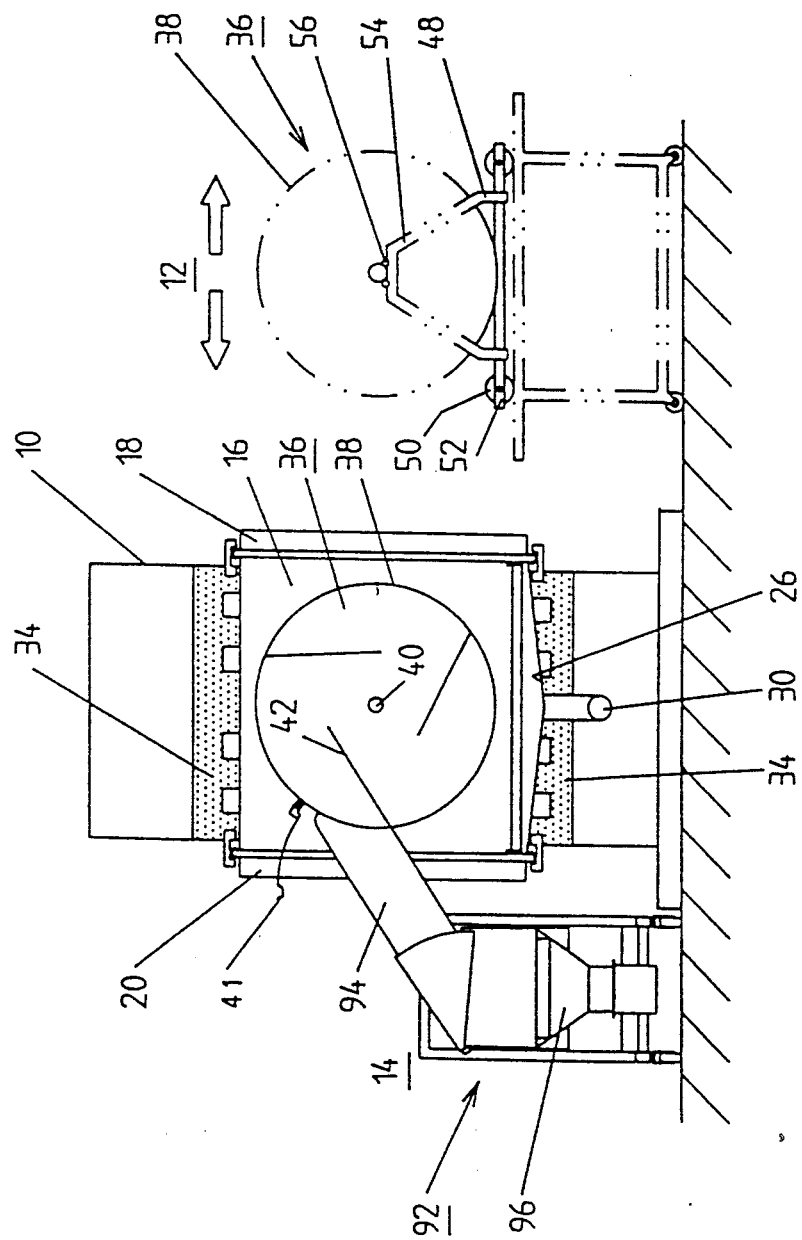
FIG. 6 is a schematic partial sectional view corresponding to that of FIG. 1, of a further embodiment of the invention.

The preferred embodiment of the invention as shown in FIGS. 6 and 7 substantially corresponds to that shown in FIGS. 1 to 5, the same reference numerals being used for equivalent components. The apparatus according to FIGS. 6 and 7 differs from that shown in FIGS. 1 to 5 to advantage in that the frame 48 mounting the drum 38 when moved into the autoclave chamber 16 can be released from the drum and independently of the latter, can be removed from the autoclave chamber. The frame 48 is thus located during cleaning, outside of the autoclave chamber where it cannot constitute a source of contamination in the autoclave chamber.

Uncoupling the frame from the drum, after the drum shaft has been coupled to the drive and the counterbearing, can be done in various ways as will now be explained with reference to FIG. 7.

FIG. 7 shows the ends of the drum shaft 40 in axial cross section. The right-hand drive shaft end shown in FIG. 7 is substantially the same as that shown in FIG. 4 except that the hollow shaft 62 can be shifted axially in the usual way b means of a pneumatic cylinder (not shown) and the like. The left-hand end of the drum shaft shown in FIG. 7 features, the same as the right-hand end, a taper stub coupling end 80a which mates with a complementary coupling end 82a which is permanently connected to the axial shifting shaft 100. In addition, the drum shaft has at its left-hand end a further bearing disk 58a running on the rollers 56a of a bracket 54a located, like the bracket 54, at the other end of the frame.

The coupling ends 82, 82a are retracted when the drum is moved in and out of the autoclave chamber so that the coupling ends 80 and 80a respectively are released and the driven pin 86 is disengaged. After the drum has been moved into the autoclave chamber by means of the frame such as frame 48, the coupling ends 80, 80a are forced inwards to mate with the coupling ends 82, 82a which are located somewhat lower, so that the drum shaft is lifted when the coupling ends are forced further inwards. Alternatively or additionally the rollers 56, 56a can be configured lowerable, e.g. by the brackets 54 having in the vicinity of the rollers 56, 56a a joint (not shown) and by the angle between the arms of the brackets 54 being alterable by means of a spindle or means having the same effect (not shown) so that the rollers are lowered and lifted respectively when the brackets are extended and contracted, as indicated by the double arrows below the brackets 54, 54s shown merely in part in FIG. 7.

The embodiments as described can be modified in many ways.

The nozzle pipe 44 can have nozzles spraying both inwards and outwards, as shown in FIG. 5, which is particularly useful when the nozzle pipe 44 is connected to the drive shaft 62 and is intended to serve both for cleaning the interior wall of the autoclave chamber and for cleaning the objects in the autoclave chamber.

The autoclave chamber 16 can have the shape of a drum or cylinder, i.e. instead of the enclosure wall formed by the sidewalls, the floor and the top wall, a cylindrical or tubular shaped enclosure wall is provided.

The cleaning drum can also be designed to accept cassettes or be replaced by a suitably designed frame.

Instead of the driven pin 86 the coupling ends 80, 82 can be provided toothed to provide a positive-drive coupling.

What is claimed is:

1. An apparatus for cleaning and sterilizing objects, comprising:
   an autoclave chamber having a loading opening in a first wall thereof, first closure means for sealing off said loading opening in said first wall, an unloading opening in a second wall thereof, opposite said first wall, second closure means for sealing off said unloading opening, and first and second end walls;
   cleaning means provided with means for moving said cleaning means into and out of said autoclave chamber, said cleaning means including a frame, a drum mounted on said frame and receiving objects to be cleaned and having a foraminous circumferential wall, and a hollow drum shaft for rotatably mounting the drum on the frame, said drum shaft having spraying nozzles in a wall thereof; and
   a hollow drive shaft engageably-disengageable from the hollow drum shaft and passing through the first end wall of the autoclave chamber, said drive shaft being rotatably mounted to and sealed with respect to said first end wall and having connecting means outside of said autoclave chamber for connecting said drive shaft to a driving unit;
   said drive shaft and said drum shaft each being provided with one of a pair of mutually complementary first coupling means for mechanically coupling said drive shaft to said drum shaft,
   said drum shaft and said drive shaft each having a fluid channel running therethrough, said fluid channel of said drive shaft receiving fluid from an outside source,
   said first coupling means being constructed so as to connect said fluid channel of said drive shaft to said fluid channel of said drum shaft when said drum shaft and said drive shaft are mechanically coupled to each other so that said drum shaft conveys cleaning fluid to be sprayed by said spraying nozzles into said autoclave chamber when said cleaning means is in said autoclave chamber.

2. An apparatus according to claim 1, further comprising a pair of mutually complementary second coupling means mounted on a portion of the drum shaft (40) facing away from the drive shaft, and on said second end wall, respectively.

3. An apparatus according to claim 2, wherein said moving means introduce the frame with the drum through the loading opening into the autoclave chamber and remove the frame without the drum from the autoclave chamber through the loading opening.

4. An apparatus according to claim 1, wherein said first coupling means have substantially tapered end coupling surfaces which are coupled to each other and uncoupled from each other by an axial shifting in relation to each other.

5. An apparatus according to claim 1, wherein said frame is removable from the autoclave chamber independently of said drum when the drum shaft is coupled to the drive shaft.

6. An apparatus according to claim 1, and further comprising a bearing disk mounted on said drum shaft at least at an end thereof facing the drive shaft, and rollers mounted in the frame, said bearing disc being rotatably supported by said rollers when said drum shaft is uncoupled from said drive shaft and being lifted off said rollers when the drum shaft is coupled to the drive shaft.

7. An apparatus according to claim 1, wherein the nozzles of the drum shaft are oriented to face radially outwards and the drum comprises baffle plates which extend essentially axially from an inner side of a circumferential wall of the drum inwards in directions which form an angle with a radial direction.

8. An apparatus according to claim 1, and further comprising a nozzled pipe connected to a part of the drive shaft projecting into the autoclave chamber.

9. An apparatus according to claim 8, wherein the nozzles pipe has nozzles oriented radially outwards.

10. An apparatus according to claim 8, wherein the nozzle pipe has nozzles oriented radially inwards.

11. An apparatus according to claim 1, wherein the drum shaft and the drive shaft each includes at least two fluid channels and the drive shaft has means at an outer end thereof for introducing cleaning fluid into said at least two channels.

12. An apparatus according to claim 1, and further comprising means for introducing microwaves into said autoclave chamber.

13. An apparatus according to claim 1, wherein the autoclave chamber has an internal wall provided with nozzles oriented into an interior of the autoclave chamber.

14. An apparatus according to claim 1, and further comprising a counter-bearing shaft mounted in said second end wall of the autoclave chamber opposite the drive shaft, and means connected to said counter-bearing shaft for coupling said counter-bearing shaft with the drum shaft.

15. An apparatus according to claim 14, wherein the counter-bearing shaft is a hollow shaft having at least one fluid channel and having means for feeding fluid into said at least one fluid channel.

16. An apparatus according to claim 14, and further comprising means mounted on said counter-bearing shaft and coupled to rotary drive means.

17. An apparatus for cleaning and sterilizing objects, comprising:
   an autoclave chamber having a loading opening in a first wall thereof, first closure means for sealing off said loading opening in said first wall, an unloading opening in a second wall thereof opposite said first wall, second closure means for sealing off said unloading opening, and first and second end walls;
   cleaning means including a frame, a drum mounted on said frame and receiving objects to be cleaned and having a foraminous circumferential wall, means to removably insert said drum in said chamber, and a hollow drum shaft for rotatably mounting the drum on the frame, said drum shaft having spraying nozzles in a wall thereof;
   a hollow drive shaft engageably-disengageable from the hollow drum shaft and passing through the first end wall of the autoclave chamber, said drive shaft being rotatably mounted to and sealed with respect to said first end wall and having connecting means outside of said autoclave chamber for connecting said drive shaft to a driving unit;
   said drive shaft and said drum shaft each being provided with one of a pair of mutually complementary first coupling means for mechanically coupling said drive shaft to said drum shaft,
   said frame being removable from the autoclave chamber independently from said drum when said drum shaft is coupled to said drive shaft,
   said hollow drum shaft and said drive shaft each having a fluid channel running therethrough, said fluid channel of said drive channel receiving cleaning fluid from an outside source, said first coupling means being constructed so as to connect said fluid channel of said drive shaft to said fluid channel of said drum shaft when said drum shaft and said drive shaft are mechanically coupled to each other so that said drum shaft conveys cleaning fluid to be sprayed by said spraying nozzles into said autoclave chamber when said cleaning means is in said autoclave chamber.

* * * * *